US00PP15679P3

(12) United States Plant Patent
Trees

(10) Patent No.: US PP15,679 P3
(45) Date of Patent: Mar. 15, 2005

(54) ***GERANIUM* PLANT NAMED 'BALFANSAL'**

(50) Latin Name: *Pelargonium×hortorum*
Varietal Denomination: Balfansal

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 3 days.

(21) Appl. No.: 10/741,010

(22) Filed: Dec. 19, 2003

(65) Prior Publication Data

US 2004/0226068 P1 Nov. 11, 2004

(51) Int. Cl.[7] ..... A01H 5/00
(52) U.S. Cl. ..... Plt./327
(58) Field of Search ..... Plt./327

*Primary Examiner*—Kent Bell
(74) *Attorney, Agent, or Firm*—Wood, Phillips, Katz, Clark & Mortimer

(57) ABSTRACT

A new and distinct cultivar of *Geranium* plant named 'Balfansal', characterized by its semi-double salmon-colored flowers, dark green-colored foliage, and vigorous, upright and mounded growth habit.

2 Drawing Sheets

Latin name of genus and species of plant claimed: *Pelargonium×hortorum.*
Variety denomination: 'Balfansal'.

BACKGROUND OF THE INVENTION

The present invention relates to a new and distinct cultivar of *Geranium* plant botanically known as *Pelargonium× hortorum* and hereinafter referred to by the cultivar name 'Balfansal'.

The new cultivar originated in a controlled breeding program in Arroyo Grande, Calif., during 2000. The purpose of the breeding program was the creation of *Geranium* plants with a vigorous, upright mounded growth habit, dark green-colored foliage, and new and unique flower color.

The female parent of 'Balfansal' was 'BFP-445 Salmon' (U.S. Plant Pat. No. 9,228). The male parent of 'Balfansal' was 'Fishelen' (U.S. Plant Pat. No. 12,727). The new *Geranium* was discovered and selected by the inventor as a single flowering plant from within the progeny of the above stated cross-pollination during August 2001 at Arroyo Grande, Calif. and was initially designated '2810-38'.

Asexual reproduction of the new cultivar by terminal stem cuttings taken since August 2001 at Arroyo Grande, Calif. and West Chicago, Ill., has demonstrated that the new cultivar reproduces true to type with all characteristics, as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment, such as temperature, light intensity, and day length, without, however, any variance in genotype.

It was repeatedly found that the cultivar of the present invention:

1. Forms semi-double salmon-colored flowers,
2. Forms dark green-colored foliage, and
3. Exhibits a vigorous, upright and mounded growth habit.

Plants of the new cultivar have a less compact habit and have more petals per flower than plants of the female parent. Plants of the new cultivar have darker green-colored foliage than plants of the male parent. Plants of the new cultivar have flowers that are uniformly semi-double, whereas the flowers of the male parent are weakly semi-double.

Of the many commercially available *Geranium* cultivars known to the inventor, the most similar in comparison to 'Balfansal' is 'Balfansami' (U.S. Plant Pat. No. 11,764). However, in side by side comparisons, plants of 'Balfansal' differ from plants of 'Balfansami' in the following characteristics:

1. Plants of 'Balfansal' exhibit darker flower color than plants of 'Balfansami', and
2. Plants of 'Balfansal' exhibit a more distinct leaf zonation than plants of 'Belfansami'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balfansal'. The plants were grown for 8 weeks in a greenhouse at West Chicago, Ill.

DETAILED BOTANICAL DESCRIPTION

Figure 1:
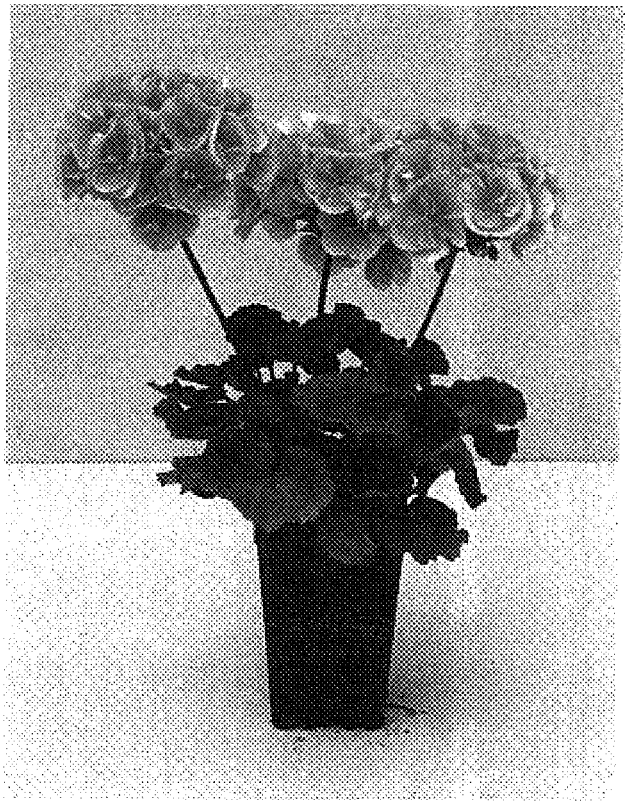
FIG. 1 illustrates a side view of the overall growth and flowering habit of 'Balfansal'.
Figure 2:
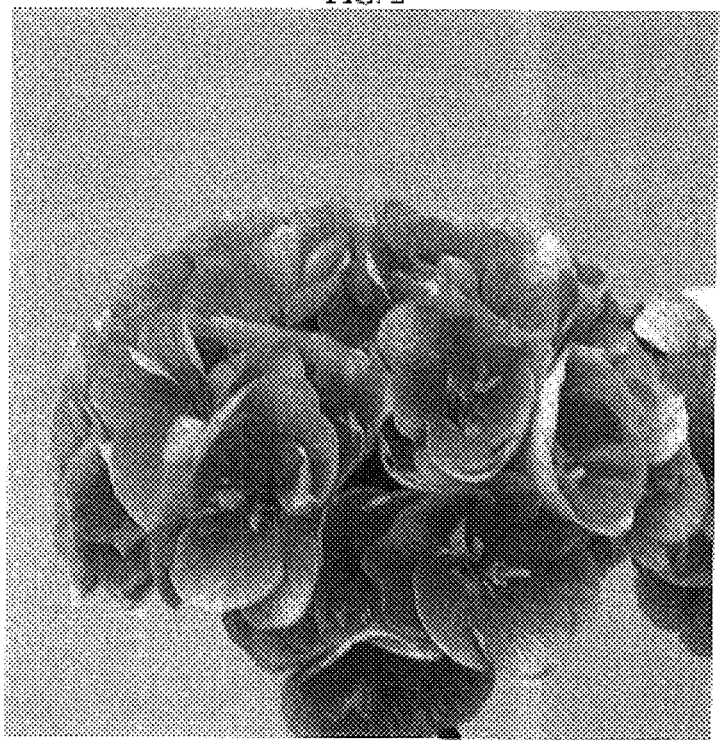
FIG. 2 illustrates a close-up view of a single umbel of 'Balfansal'.
Figure 3:
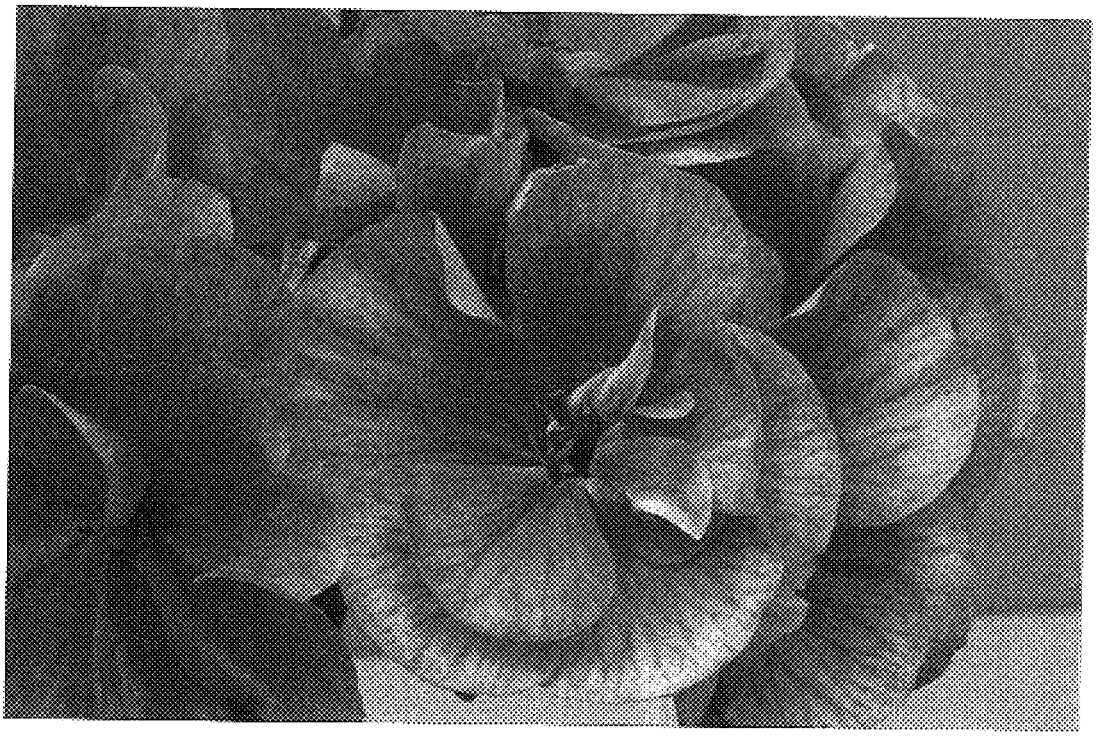
FIG. 3 illustrates a close-up view of single flowers 'Balfansal'.

The chart used in the identification of colors described herein is the R.H.S. Colour Chart of The Royal Horticultural Society, London, England, 1995 edition, except where general color terms of ordinary significance are used. The color values were determined on Jul. 30, 2003 in West Chicago, Ill. The readings were taken between 10:00 and 11:45 a.m. under natural light conditions.

The plants used for the following measurements and descriptions were produced from cuttings taken from stock plants and grown in a double polycarbonate-covered greenhouse in West Chicago, Ill. under conditions comparable to those used in commercial practice. The plants were grown in 10 cm pots for 8 weeks utilizing a soilless growth medium. Greenhouse temperatures were maintained at approximately 65°–70° F. (18°–21° C.) during the day and approximately 60°–65° F. (15°–18° C.) during the night. Greenhouse light levels of 4,000–6,000 footcandles were maintained during the day. Plants were pinched at three weeks after the planting of a rooted cutting.

Botanical classification: *Pelargonium×hortorum* cultivar 'Balfansal'.

Parentage:

*Female parent.*—'BFP-445 Salmon' (U.S. Plant Pat. No. 9,228).

*Male parent.*—'Fishelen' (U.S. Plant Pat. No. 12,727).

Propagation:

*Type cutting.*—Terminal stem.

*Time to initiate roots.*—Approximately 10 to 14 days.

*Time to develop roots.*—Approximately 21 to 28 days.

*Root description.*—Fibrous.

*Rooting habit.*—Well branched.

Plant description:

*Growth habit and general appearance.*—Vigorous, upright and mounded.

*Height above pot.*—Without inflorescences: Approximately 13.4 cm. Including inflorescences: Approximately 24.2 cm.

*Width/area of spread.*—Approximately 23.8 cm.

*Branching habit.*—Freely basal branching. Approximately 2 branches per plant. Pinching 14 to 21 days after transplanting helps to improve basal branching.

*Branch description.*—Length: Approximately 13.8 cm. Diameter: Approximately 8 mm. Color: 144A. Texture: Hirsute. Internode length at center of branch: Approximately 1.7 cm.

*Foliage description.*—Form: Mature foliage is simple. Arrangement: Opposite. Number of leaves per lateral branch: Approximately 10. Shape: Reniform. Margin: Crenate. Apex: Rounded. Base: Cordate. Venation pattern: Palmate. Upper surface texture: Moderately pubescent. Lower surface texture: Moderately pubescent with dense pubescence along veins. Color of mature foliage: Upper surface: 137A with veins of 145A and zone of 147A. Color of mature foliage: Lower surface: 137C with veins of 146A. Size: Mature leaf length: Approximately 4.6 cm. Mature leaf width: Approximately 7.9 cm. Petiole length: Approximately 6.3 cm. Petiole diameter: Approximately 2.7 mm. Petiole Texture: Pubescent on both upper and lower surface. Petiole color: 146B with overlay of 187B on upper surface.

Flowering description:

*Outdoor flowering habit.*—'Balfansal' is freely flowering under outdoor growing conditions with substantially continuous blooming from spring through fall.

*Time of first flower.*—Approximately 8 weeks after planting of rooted cutting.

*Lastingness of individual bloom.*—Approximately 5–7 days.

Inflorescence description:

*Type.*—Hemispherical umbel. Position: Above foliage. Number of open umbels at any one time: 2. Number of developing umbels at any one time: 2. Umbel diameter: Approximately 12.1 cm. Umbel height/depth: Approximately 6.9 cm. Number of flowers per umbel: Approximately 15.6.

*Peduncle.*—Strong, erect. Length: Approximately 13.9 cm. Diameter: Approximately 4 mm. Texture: Puberulent. Color: 143D at base with rest of length overlaid with 187A.

Flower description:

*Bud just before opening.*—Shape: Elliptic. Length: Approximately 1.4 cm. Diameter: Approximately 7.3 mm. Petal color: 38C. Sepal color: N144C.

*Corolla.*—Form: Semi-double. Shape: Round, slightly cupped. Diameter/Width: Approximately 4.7 cm. Depth: Approximately 1.5 cm. Fragrance: None. Persistent.

*Petals/petaloids.*—Quantity: Approximately 8 petals and 4 petaloids per flower. Arrangement: Imbricate. Shape: Obovate. Apex: Obtuse. Base: Attenuate. Margin: Entire. Texture of upper and lower surface: Glabrous. Upper petal length: Approximately 2.3 cm. Upper petal width: Approximately 2 cm. Lower petal length: Approximately 2.5 cm. Lower petal width: Approximately 1.5 cm. Color of all petals: Fully opened, upper surface: 52A with 55B at margin and venation of 46D. Lower petals are N155B at base. Color all petals: Fully opened, lower surface: N155D with venation of 46D. Petaloid characteristics are the same as the petals.

*Pedicel.*—Strength: Strong. Angle: Erect. Length: Approximately 4 cm. Diameter: Approximately 1.4 mm. Texture: Soft, short dense hairs. Color: 144C with overlay of 180B.

*Sepals.*—Quantity per flower: 5. Shape: Elliptic. Tip: Acuminate. Base: Truncate. Margin: Entire. Length of largest sepal: 1.1 cm. Width of largest sepal: 3 mm. Length of smallest sepal: 1.1 cm. Width of smallest sepal: 2 mm. Texture: Upper surface (inside): Glabrous. Lower surface (outside): Puberulent. Color: Upper and lower surface: N144C with overlay of 185A at base.

*Reproductive organs.*—Androecium: Stamen number: 5 per flower. Filament quantity: Approximately 11. Filament color: N155B. Anther quantity: Approximately 9. Anther length: Approximately 2 mm. Immature anther color: 52B. Mature anther color: 61B. Pollen amount: Moderate. Pollen color 169A. Gynoecium: Pistil quantity: One per flower. Pistil length: Approximately 9 mm. Stigma shape: 5 pointed star. Stigma length: 2 mm. Stigma color: 45D. Style length: 2 mm. Style color: 45D. Ovary length: 5 mm. Ovary diameter: 2 mm. Ovary texture: Sericeous. Ovary color: 143C.

Seed and fruit production: Neither seed nor fruit production has been observed.

Disease and pest resistance: Resistance to pathogens and pests common to *Geraniums* has not been observed.

Hardiness zone: 'Balfansal' is hardy in zones nine (9) and above.

What is claimed is:

1. A new and distinct cultivar of *Geranium* plant named 'Balfansal', substantially, as herein shown and described, which:

1. Forms semi-double salmon-colored flowers,
2. Forms dark green-colored foliage, and
3. Exhibits a vigorous, upright and mounded growth habit.

* * * * *